United States Patent [19]

Katz

[11] 4,237,159

[45] Dec. 2, 1980

[54] NOVEL ANTI-INFLAMMATORY COMPOSITION

[76] Inventor: Laurence B. Katz, A901 Presidential Apts., City Line Ave. & Presidential Blvd., Philadelphia, Pa. 19131

[21] Appl. No.: 95,235

[22] Filed: Nov. 19, 1979

[51] Int. Cl.³ ............................................. A61K 31/40
[52] U.S. Cl. .................................................... 424/274
[58] Field of Search ......................................... 424/274

[56] References Cited

PUBLICATIONS

Chem. Abst., 9th Coll. Index (Subject) Proseodymium 2-Propenenitrile, p. 31773cs.
Chem. Abst. 81-163333x (1974).
Merck Index, 9th ed. (1976) p. 656.

*Primary Examiner*—Stanley J. Friedman
*Attorney, Agent, or Firm*—Walter Katz

[57] ABSTRACT

The anti-inflammatory activity of non-steroidal anti-inflammatory agents are potentiated by the admixture with cinanserin, a compound which does not exhibit any anti-edema properties.

4 Claims, 1 Drawing Figure

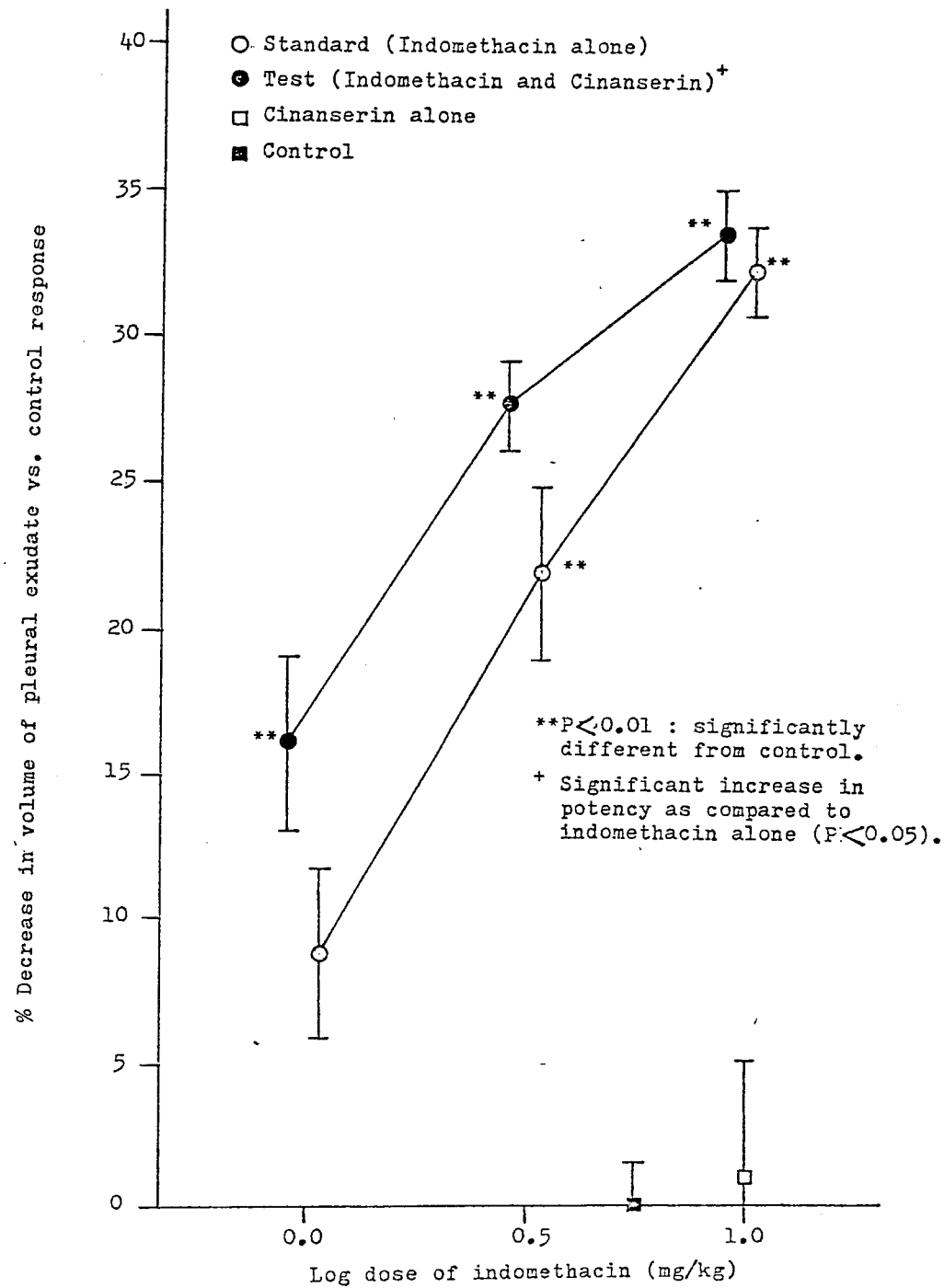

NOVEL ANTI-INFLAMMATORY COMPOSITION

BACKGROUND OF THE INVENTION

1. Field of the Invention

The present invention is related to pharmaceutical compositions useful for treating inflammation, and, particularly, to the potentiation of the activity of non-steroidal anti-inflammatory agents with cinanserin, a compound without anti-edema properties of its own.

2. Description of the Prior Art

A major drawback to the treatment of inflammatory conditions with orally active non-steroidal anti-inflammatory drugs (NSAID) is the degree of gastric intolerance, bleeding, erosions and ulceration caused by this group of compounds, Boyle, E. et al, J. Pharm. Pharmac., 28, 865 (1976). Removal of this irritation by use of a combination of drugs to allow reduction of dosage without sacrificing clinical efficacy would constitute a significant therapeutic advance. However, simultaneous administration of two or more NSAID has not been found to produce an anti-inflammatory (AI) effect greater than that produced by either of them given alone at the same dose, Swingle, K. et al. J. Pharmacol. Exp. Ther. 172, 423 (1970).

Accordingly, it is an object of this invention to potentiate the AI activity of a NSAID, such as indomethacin, by the simultaneous administration of a pharmacological compound which itself does not exhibit anti-edema properties, no matter how high the dose employed. In order for potentiation to be properly demonstrated, a drug without effect of its own must be shown to enhance the effect of an active drug, when the two are given together.

SUMMARY OF THE INVENTION

What is described herein is a pharmaceutical composition useful for treating inflammation in humans and animals which comprises an anti-inflammatory amount of a non-steroidal anti-inflammatory agent potentiated by being admixed with cinanserin, a pharmacological compound which itself does not exhibit anti-edema properties. In the preferred form of the invention, the combination of indomethacin and cinanserin provides a significant potentiation of the anti-inflammatory effect of idomethacin alone.

IN THE DRAWINGS

The FIGURE is a graphical representation of the anti-edma activity of indomethacin alone and in combination with cinanserin.

DETAILED DESCRIPTION OF THE INVENTION

The composition of the present invention normally is adapted for oral administration and, accordingly, may be presented as any conventional dosage form such as tablets, capsules, sachets of reconstitutable powder or the like. Most suitably the composition is in the form of a unit dose containing 20-200 mg. of the NSAID, e.g. 25 to 50 mg. and about 5-100 mg. of cinanserin, e.g. 10-50 mg. A preferred ratio of NSAID to cinanserin in a unit dose ranges from about 2:1 to 5:1. Such compositions may be administered once or more times per day so that the total daily dose for a 70 kg adult will be in the order of about 50-200 mg, for example, 75-150 mg. of the NSAID, and about 10-100 mg, for example, 25-50 mg. of cinanserin.

The compositions may be prepared in conventional manner by mixing, filling, tabletting and the like and the compositions may contain conventional excipients such as lubricants, desintegrants, binders, fillers, coloring agents, flavors and the like.

Typical NSAID agents include indomethacin, naproxen, ketoprofen, phenylbutazone and the like. The following description will be made with particular reference to indomethacin.

Cinanserin is the chemical compound 2'-(3'dimethylaminopropylthio) cinnamanilide hydrochloride.

PHARMACOLOGY

The potentiation interaction between cinanserin and indomethacin was substantiated using the reduction of carrageenin induced edema in the pleural edema test on rats weighing about 330 g. as the test animal. A fixed dose of 31.6 mg/kg of cinanserin in combination with three dosage levels of indomethacin, 1 mg/kg, 3.16 mg/kg and 10 mg/kg was administered orally in the tests. No significant activity was observed for cinanserin alone at any dosage level, even as high as 360 mg/kg of the drug, in reduction of inflammation.

The experimental results are given in the Table below and in the graphical representation in the FIGURE. They show a significant increase in potency for the combination of indomethacin and cinanserin as compared to indomethacin alone.

TABLE

Comparison of Anti-edema Activity of Indomethacin Alone and in Combination with Cinanserin in Rat Pleural Edema

| Preparation | Cont.[a] | Standard(Ind.[b]alone) | | | Cin.[c] | Test[d](Ind. and Cin.)* | | |
|---|---|---|---|---|---|---|---|---|
| Dose (mg/kg) | — | 1.0 | 3.16 | 10.0 | 31.6 | 1.0 | 3.16 | 10.0 |
| Volume of Exudate (ml) | 6.9 Pleural | 6.3 | 5.4 | 4.7 | 6.8 | 5.8 | 5.0 | 4.6 |
| % Change from | — | −8.7 | −21.7 | −31.9 | −1.4 | −15.9 | −27.5 | −33.3 |

TABLE-continued

Comparison of Anti-edema Activity of Indomethacin Alone and in Combination with Cinanserin in Rat Pleural Edema

| Preparation | Cont.[a] | Standard(Ind.[b] alone) | Cin.[c] | Test[d](Ind. and Cin.)* |
|---|---|---|---|---|
| Cont. | | | | |

[a]Cont. = Control rats received 1 ml/100 g of the vehicle (0.5% tragacanth).
[b]Ind. = Indomethacin
[c]Cin. = Cinanserin
[d]Test preparation consisted of the stated dose of indomethacin plus 31.6 mg/kg of cinanserin in a total volume equal to that of the standard preparation.
*Significantly more potent than the standard preparation.

What is claimed is:

1. A pharmaceutical composition useful for treating inflammation in humans and animals which comprises indomethacin and cinanserin in oral dosage form, each dosage unit of which contains from 20 to 200 mg. of indomethacin and from 5 to 100 mg. of cinanserin.

2. A composition according to claim 1, each dosage unit of which contains from 25 to 50 mg. of indomethacin and from 10 to 50 mg. of cinanserin.

3. A composition according to claim 1, each dosage unit of which contains indomethacin and cinanserin in a ratio of about 2:1 to about 5:1 in parts by weight.

4. A method of treating inflammation in humans and animals which comprises orally administering the composition of claims 1, 2 or 3.